US008729336B2

(12) United States Patent
Flexner et al.

(10) Patent No.: US 8,729,336 B2
(45) Date of Patent: May 20, 2014

(54) PROTEIN MIXTURES FOR MAIZE INSECT CONTROL

(75) Inventors: John L. Flexner, Landenberg, PA (US); Deirdre M. Kapka-Kitzman, Ankeny, IA (US); Lisa Procyk, Ankeny, IA (US); Bruce Stanley, Wilmington, DE (US); Jianzhou Zhao, Johnston, IA (US)

(73) Assignees: Pioneer Hi-Bred International, Inc, Johnston, IA (US); E.I. du Pont de Nemours and Company, Wilmington, DE (US)

( * ) Notice: Subject to any disclaimer, the term of this patent is extended or adjusted under 35 U.S.C. 154(b) by 719 days.

(21) Appl. No.: 12/691,841

(22) Filed: Jan. 22, 2010

(65) Prior Publication Data

US 2010/0221238 A1 Sep. 2, 2010

Related U.S. Application Data

(60) Provisional application No. 61/146,875, filed on Jan. 23, 2009.

(51) Int. Cl.

| | |
|---|---|
| ***A01H 5/00*** | (2006.01) |
| ***C07K 14/325*** | (2006.01) |
| ***A01N 37/18*** | (2006.01) |
| ***C12N 15/32*** | (2006.01) |
| ***C12N 15/82*** | (2006.01) |

(52) U.S. Cl.

USPC ........ 800/279; 800/302; 800/320.1; 435/418; 435/468; 514/4.5; 536/23.71

(58) Field of Classification Search

None

See application file for complete search history.

(56) References Cited

U.S. PATENT DOCUMENTS

| | | | | |
|---|---|---|---|---|
| 7,208,474 | B2 | 4/2007 | Bermudez et al. | |
| 2005/0204421 | A1 * | 9/2005 | Bermudez et al. ............ | 800/279 |
| 2007/0204369 | A1 | 8/2007 | Bermudez et al. | |
| 2009/0226998 | A1 | 9/2009 | Cerf et al. | |
| 2010/0269221 | A1 * | 10/2010 | Abad et al. .................... | 800/279 |

FOREIGN PATENT DOCUMENTS

| | | | |
|---|---|---|---|
| CN | 1614022 | | 5/2005 |
| WO | WO 02/098911 | A2 | 12/2002 |
| WO | WO 2008/073877 | A2 | 6/2008 |

OTHER PUBLICATIONS

Tounsi et al (J. Appl. MicrobioL 95:23-28; 2003).*
de Maagd et al (Appl Environ. Microbiol 65:4369-4374, 1999).*
Aronson et al (FEMS Microbiol. Lett. 2001, 195:1-8).*
Friedberg (Brief. Bioinformatics (2006) 7: 225-242).*
Castle et al (Current Opinion in Biotechnology 2006. 17: 105-112).*
Tang et al (Mol. Breeding, 2006, 18:1-10).*
Colby et al., "Calculating Synergistic and Antagonistic Responses of Herbicide Combinations," *Weeds*, 1967, vol. 15(1), pp. 20-22.
Ding et al., "Expression and synergism of two cry insecticidal protein genes in *P. fluorescens*," *Acta Microbiologica Sinica.*, 2000, vol. 40(6), pp. 573-578, Abstract Only (p. 578).
Liao et al., Toxicity of *Bacillus thuringiensis* insecticidal proteins for *Helicoverpa armigera* and *Helicoverpa puncitgera* (Lepidoptera: Noctuidae),major pests of cotton, *Journal of Invertebrate Pathology*, 2002, vol. 80, pp. 55-63.
Anonymous, "Bollgard II: A New Generation of Bt Genes Commercialized," *The ICAC recorder*, Mar. 2003, pp. 3-10, vol. 21(1).
Colby, S.R.; "Calculating Synerdistic and Antagonistic Responses of Herbicide Combinations", Weeds. vol. 15, No. 1, p. 1 20-22 (1957).
Tabashnik.B.E.; "Evaluation of synergism among Bacillus thuringiensis toxins". Appl. Environ. Microbiol. vol. 58 (10); 3343-3346 (1992).

* cited by examiner

*Primary Examiner* — Anne Kubelik
*Assistant Examiner* — Lee A Visone
(74) *Attorney, Agent, or Firm* — Pioneer Hi-Bred International, Inc

(57) ABSTRACT

Embodiments of the present invention relate to insecticidal *Bacillus thuringiensis* Cry1 and Cry2 polypeptides. Methods for using the polypeptides and nucleic acids of embodiments of the invention to synergistically enhance resistance of plants to insect predation are encompassed in embodiments of the present invention.

15 Claims, 2 Drawing Sheets

>IP1-88 (SEQ ID NO:1)
MGHNNPNINECIPYNCLSNPEVEVLGGERIETGYTPIDISLSLTQFLLSEFVPGAGFVLGLV
DVIWGIFGPSQWDAFLVQIEQLINQRIEEFARNQAISRVEGLSNLYQIYAESFREWEADPTN
PALKEEMRTQFNDMNSALTTAIPLFAVQNYQVPLLSVYVQAANLHLSVLRDVSVFGQRWGFD
AATINSRYNDLTRLIGNYTDHAVRWHNTGLERIWGPDSRDWIRYNQFRRELTLTVLDIVSLF
PNYDSRTYPIRTASQLTREIYTNPVLENFDGSFRGSAQGIEGSIRSPHLMDILNSITIYTDA
HRGEYYWSGHQIMASPVGFSGPEFTFPLYGTMGNAAPQQRIVAQLGQGVYRTLSSTLYRRPF
NIGINNQQLSVLDGTEFAYGTSSNLPSAVYRKSGTVDSLDEIPPQNNNVPPRQGFSHRLSHV
SMFRSGFSNSSVSIIRAPMFSWIHRSAEFNNTIDPERINQIPLTKSTNLGSGTSVVKGPGFT
GGDILRRTSPGQISTLRVNITAPLSQRYRVRIRYASTTNLQFHTSIDGRPINQGNFSATMSS
GSNLQSGSFRTVGFTTPFNFSNGSSVFTLSAHVFNSGNEVYIDRIEFVPAEVTFEAEYDLER
AQKVVNALFTSSNQIGLKTDVTDYHIDQVSNLVDCLSDEFCLDEKRELSEKVKHAKRLSDER
NLLQDPNFRGINRQPDRGWRGSTDITIQGGDDVFKENYVTLPGTVDECYPTYLYQKIDESKL
KAYTRYELRGYIEDSQDLEIYLIRYNAKHEIVNVPGTGSLWPLSAQSPIGKCGEPNRCAPHL
EWNPDLDCSCRDGEKCAHHSHHFTLDIDVGCTDLNEDLGVWVIFKIKTQDGHARLGNLEFLE
EKPLLGEALARVKRAEKKWRDKREKLQLETNIVYKEAKESVDALFVNSQYDRLQVDTNIAMI
HAADKRVHRIREAYLPELSVIPGVNAAIFEELEGRIFTAYSLYDARNVIKNGDFNNGLLCWN
VKGHVDVEEQNNHRSVLVIPEWEAEVSQEVRVCPGRGYILRVTAYKEGYGEGCVTIHEIEDN
TDELKFSNCVEEEVYPNNTVTCNNYTGTQEEYEGTYTSRNQGYDEAYGNNPSVPADYASVYE
EKSYTDGRRENPCESNRGYGDYTPLPAGYVTKDLEYFPETDKVWIEIGETEGTFIVDSVELL
LMEE

>IP2-127 (SEQ ID NO:2)
MGNSVLNSGRTTICDAYNVAAHDPFSFQHKSLDTVQREWTEWKKNNHSLYLDPIVGTVASFL
LKKVGSLVGKRILSELRNLIFPSGSTNLMQDILRETEQFLNQRLDTDTLARVNAELTGLQAN
VEEFNRQVDNFLNPNRNAVPLSITSSVNTMQQLFLNRLPQFQMQGYQLLLLPLFAQAANLHL
SFIRDVILNADEWGISAATLRTYRDYLKNYTRDYSNYCINTYQSAFKGLNTRLHGTLEFRTY
MFLNVFEYVSIWSLFKYQSLLVSSGANLYASGSGPQQTQSFTSQDWPFLYSLFQVNSNYVLN
GFSGARLSNTFPNIGGLPGSTTTHALLAARVNYSGGISSGDIGASPFNQNFNCSTFLPPLLT
PFVRSWLDSGSDREGVATVTNWQTESFETTLGLRSGAFTARGNSNYFPDYFIRNISGVPLVV
RNEDLRRPLHYNEIRNIASPSGTPGGARAYMVSVHNRKNNIHAVHENGSMIHLAPNDYTGFT
ISPIHATQVNNQTRTFISEKFGNQGDSLRFEQNNTTARYTLRGNGNSYNLYLRVSSIGNSTI
RVTINGRVYTATNVNTTTNNDGVNDNGARFSDINIGNVVASSNSDVPLDINVTFNSGTQFDL
MNTMLVPTNISPLY

>Cry1Ah-DNA (SEQ ID NO:3)
atggcttataataataatcaaaatcaatgcataccttataattgtttgaataatcccgaaat
cgaaatattagaaggcggaagaatatcagttggtaataccccaattgatatttctctttcgc
ttactcagtttcttttgagtgaatttgtcccaggtgcggggtttgtattaggattaattgat
ttaatatggggatttgtaggtccttcccaatgggacgcatttcttgctcaagtggaacagtt
aattaaccaaagaatagcagaagctgtaagaaatacagcaattcaggaattagagggaatgg
cacgggtttatagaacctatgctactgcttttgctgagtgggaaaaagctcctgatgaccca
gagctaagagaagcactacgtacacaatttacagcaactgagacttatataagtggaagaat
atccgttttaaaaattcaaacttttgaagtacagctgttatcagtgtttgcccaagctgcaa
atttacatttatctttattaagagacgttgtgtttttgggcaaagatggggtttttcaacg
acaaccgtaaataattactacaatgatttaacagaagggattagtacctatacagattatgc
tgtacgctggtacaatacgggattagaacgtgtatggggaccggattctagagattgggtaa
ggtataatcaatttagaagagaattaacactaactgtattagatatcgttgctctgttcccg
aattatgatagtagaagatatccaattcgaacagtttcccaattaacaagagaaatttatac aaacccagtattagaaaattttgatggtagttttcgaggctcggctcagggcatagaaagaa
gtattaggagtccacatttgatggatatacttaacagtataaccatctatacggatgctcat
aggggttattattattggtcagggcatcaaataatggcttctcctgtcggttttcggggcc
agaattcacgtttccgctatatggaaccatgggaaatgcagctccacaacaacgtattgttg
cccaactaggtcagggcgtgtatagaacattatcctctacttttatagaagaccttttaat
atagggataaataatcaacaactatctgttcttgacgggacagaatttgcttatggaacctc
ctcaaatttgccatccgctgtatacagaaaagcggaacggtagattcgctggatgaaatac
caccacagaataacaacgtgccacctaggcaaggatttagtcatcgattaagccatgtttca
atgtttcgttcaggctctagtagtagtgtaagtataataagagctcctatgttctcttggat
acatcgtagtgctgaatttaataatataattgcatcggatagtattactcaaatccctgcag
tgaagggaaactttcttttaatggttctgtaatttcaggaccaggatttactggtggggac
ttagttagattaaatagtagtggaaataacattcagaatagagggtatattgaagttccaat
tcacttcccatcgacatctaccagatatcgagttcgtgtacggtatgcttctgtaaccccga
ttcacctcaacgttaattggggtaattcatccatttttccaatacagtaccagctacagct
acgtcattagataatctacaatcaagtgattttggttattttgaaagtgccaatgcttttac
atcttcattaggtaatatagtaggtgttagaaatttagtgggactgcaggagtgataatag
acagatttgaatttattccagttactgcaacactcgaggctgaatataatctggagagagcg
cagaaggcggtggatgcgctgtttacgtctacagaccaactagggctaaaaacaaatgtaac
ggattatcatattgatcaagtgtccaatttagttacgtgtttatcggatgaatttggtctgg
atgaaaagcgagaattgtccgagaaagtcaaacatgcgaagcgactcagtgatgaacgcaat
ttactccaagattcaaatttcaaagacattaataggcaaccagaacgtgggtggggcggaat
tactccttatggaggaattagcggctag >CrylAh(SEQ ID NO:4)
MAYNNNQNQCIPYNCLNNPEIEILEGGRISVGNTPIDISLSLTQFLLSEFVPGAGFVLGLID
LIWGFVGPSQWDAFLAQVEQLINQRIAEAVRNTAIQELEGMARVYRTYATAFAEWEKAPDDP
ELREALRTQFTATETYISGRISVLKIQTFEVQLLSVFAQAANLHLSLLRDVVFFGQRWGFST
TTVNNYYNDLTEGISTYTDYAVRWYNTGLERVWGPDSRDWVRYNQFRRELTLTVLDIVALFP
NYDSRRYPIRTVSQLTREIYTNPVLENFDGSFRGSAQGIERSIRSPHLMDILNSITIYTDAH
RGYYYWSGHQIMASPVGFSGPEFTFPLYGTMGNAAPQQRIVAQLGQGVYRTLSSTFYRRPFN
IGINNQQLSVLDGTEFAYGTSSNLPSAVYRKSGTVDSLDEIPPQNNNVPPRQGFSHRLSHVS
MFRSGSSSSVSIIRAPMFSWIHRSAEFNNIIASDSITQIPAVKGNFLFNGSVISGPGFTGGD
LVRLNSSGNNIQNRGYIEVPIHFPSTSTRYRVRVRYASVTPIHLNVNWGNSSIFSNTVPATA
TSLDNLQSSDFGYFESANAFTSSLGNIVGVRNFSGTAGVIIDRFEFIPVTATLEAEYNLERA
QKAVDALFTSTDQLGLKTNVTDYHIDQVSNLVTCLSDEFGLDEKRELSEKVKHAKRLSDERN
LLQDSNFKDINRQPERGWGGITPYGGISG

(CONTINUED)

SEQUENCE LISTING

<160> NUMBER OF SEQ ID NOS: 4

<210> SEQ ID NO 1
<211> LENGTH: 1182
<212> TYPE: PRT
<213> ORGANISM: Artificial Sequence
<220> FEATURE:
<223> OTHER INFORMATION: Cry-1-derived polypeptide

<400> SEQUENCE: 1

Met Gly His Asn Asn Pro Asn Ile Asn Glu Cys Ile Pro Tyr Asn Cys
1               5                   10                  15

Leu Ser Asn Pro Glu Val Glu Val Leu Gly Gly Glu Arg Ile Glu Thr
            20                  25                  30

Gly Tyr Thr Pro Ile Asp Ile Ser Leu Ser Leu Thr Gln Phe Leu Leu

-continued

```
        35                  40                  45

Ser Glu Phe Val Pro Gly Ala Gly Phe Val Leu Gly Leu Val Asp Val
    50                  55                  60

Ile Trp Gly Ile Phe Gly Pro Ser Gln Trp Asp Ala Phe Leu Val Gln
65                  70                  75                  80

Ile Glu Gln Leu Ile Asn Gln Arg Ile Glu Glu Phe Ala Arg Asn Gln
                85                  90                  95

Ala Ile Ser Arg Val Glu Gly Leu Ser Asn Leu Tyr Gln Ile Tyr Ala
            100                 105                 110

Glu Ser Phe Arg Glu Trp Glu Ala Asp Pro Thr Asn Pro Ala Leu Lys
        115                 120                 125

Glu Glu Met Arg Thr Gln Phe Asn Asp Met Asn Ser Ala Leu Thr Thr
    130                 135                 140

Ala Ile Pro Leu Phe Ala Val Gln Asn Tyr Gln Val Pro Leu Leu Ser
145                 150                 155                 160

Val Tyr Val Gln Ala Ala Asn Leu His Leu Ser Val Leu Arg Asp Val
                165                 170                 175

Ser Val Phe Gly Gln Arg Trp Gly Phe Asp Ala Ala Thr Ile Asn Ser
            180                 185                 190

Arg Tyr Asn Asp Leu Thr Arg Leu Ile Gly Asn Tyr Thr Asp His Ala
        195                 200                 205

Val Arg Trp His Asn Thr Gly Leu Glu Arg Ile Trp Gly Pro Asp Ser
    210                 215                 220

Arg Asp Trp Ile Arg Tyr Asn Gln Phe Arg Arg Glu Leu Thr Leu Thr
225                 230                 235                 240

Val Leu Asp Ile Val Ser Leu Phe Pro Asn Tyr Asp Ser Arg Thr Tyr
                245                 250                 255

Pro Ile Arg Thr Ala Ser Gln Leu Thr Arg Glu Ile Tyr Thr Asn Pro
            260                 265                 270

Val Leu Glu Asn Phe Asp Gly Ser Phe Arg Gly Ser Ala Gln Gly Ile
        275                 280                 285

Glu Gly Ser Ile Arg Ser Pro His Leu Met Asp Ile Leu Asn Ser Ile
    290                 295                 300

Thr Ile Tyr Thr Asp Ala His Arg Gly Glu Tyr Tyr Trp Ser Gly His
305                 310                 315                 320

Gln Ile Met Ala Ser Pro Val Gly Phe Ser Gly Pro Glu Phe Thr Phe
                325                 330                 335

Pro Leu Tyr Gly Thr Met Gly Asn Ala Ala Pro Gln Gln Arg Ile Val
            340                 345                 350

Ala Gln Leu Gly Gln Gly Val Tyr Arg Thr Leu Ser Ser Thr Leu Tyr
        355                 360                 365

Arg Arg Pro Phe Asn Ile Gly Ile Asn Asn Gln Gln Leu Ser Val Leu
    370                 375                 380

Asp Gly Thr Glu Phe Ala Tyr Gly Thr Ser Ser Asn Leu Pro Ser Ala
385                 390                 395                 400

Val Tyr Arg Lys Ser Gly Thr Val Asp Ser Leu Asp Glu Ile Pro Pro
                405                 410                 415

Gln Asn Asn Asn Val Pro Pro Arg Gln Gly Phe Ser His Arg Leu Ser
            420                 425                 430

His Val Ser Met Phe Arg Ser Gly Phe Ser Asn Ser Ser Val Ser Ile
        435                 440                 445

Ile Arg Ala Pro Met Phe Ser Trp Ile His Arg Ser Ala Glu Phe Asn
    450                 455                 460
```

-continued

```
Asn Thr Ile Asp Pro Glu Arg Ile Asn Gln Ile Pro Leu Thr Lys Ser
465                 470                 475                 480

Thr Asn Leu Gly Ser Gly Thr Ser Val Val Lys Gly Pro Gly Phe Thr
                485                 490                 495

Gly Gly Asp Ile Leu Arg Arg Thr Ser Pro Gly Gln Ile Ser Thr Leu
            500                 505                 510

Arg Val Asn Ile Thr Ala Pro Leu Ser Gln Arg Tyr Arg Val Arg Ile
        515                 520                 525

Arg Tyr Ala Ser Thr Thr Asn Leu Gln Phe His Thr Ser Ile Asp Gly
    530                 535                 540

Arg Pro Ile Asn Gln Gly Asn Phe Ser Ala Thr Met Ser Ser Gly Ser
545                 550                 555                 560

Asn Leu Gln Ser Gly Ser Phe Arg Thr Val Gly Phe Thr Thr Pro Phe
                565                 570                 575

Asn Phe Ser Asn Gly Ser Ser Val Phe Thr Leu Ser Ala His Val Phe
            580                 585                 590

Asn Ser Gly Asn Glu Val Tyr Ile Asp Arg Ile Glu Phe Val Pro Ala
        595                 600                 605

Glu Val Thr Phe Glu Ala Glu Tyr Asp Leu Glu Arg Ala Gln Lys Val
    610                 615                 620

Val Asn Ala Leu Phe Thr Ser Ser Asn Gln Ile Gly Leu Lys Thr Asp
625                 630                 635                 640

Val Thr Asp Tyr His Ile Asp Gln Val Ser Asn Leu Val Asp Cys Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Pro
        675                 680                 685

Asn Phe Arg Gly Ile Asn Arg Gln Pro Asp Arg Gly Trp Arg Gly Ser
    690                 695                 700

Thr Asp Ile Thr Ile Gln Gly Gly Asp Asp Val Phe Lys Glu Asn Tyr
705                 710                 715                 720

Val Thr Leu Pro Gly Thr Val Asp Glu Cys Tyr Pro Thr Tyr Leu Tyr
                725                 730                 735

Gln Lys Ile Asp Glu Ser Lys Leu Lys Ala Tyr Thr Arg Tyr Glu Leu
            740                 745                 750

Arg Gly Tyr Ile Glu Asp Ser Gln Asp Leu Glu Ile Tyr Leu Ile Arg
        755                 760                 765

Tyr Asn Ala Lys His Glu Ile Val Asn Val Pro Gly Thr Gly Ser Leu
    770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Thr Leu Asp
            820                 825                 830

Ile Asp Val Gly Cys Thr Asp Leu Asn Glu Asp Leu Gly Val Trp Val
        835                 840                 845

Ile Phe Lys Ile Lys Thr Gln Asp Gly His Ala Arg Leu Gly Asn Leu
    850                 855                 860

Glu Phe Leu Glu Glu Lys Pro Leu Leu Gly Glu Ala Leu Ala Arg Val
865                 870                 875                 880

Lys Arg Ala Glu Lys Lys Trp Arg Asp Lys Arg Glu Lys Leu Gln Leu
                885                 890                 895
```

```
Glu Thr Asn Ile Val Tyr Lys Glu Ala Lys Glu Ser Val Asp Ala Leu
            900                 905                 910

Phe Val Asn Ser Gln Tyr Asp Arg Leu Gln Val Asp Thr Asn Ile Ala
        915                 920                 925

Met Ile His Ala Ala Asp Lys Arg Val His Arg Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Tyr Ser Leu Tyr Asp Ala Arg
                965                 970                 975

Asn Val Ile Lys Asn Gly Asp Phe Asn Asn Gly Leu Leu Cys Trp Asn
            980                 985                 990

Val Lys Gly His Val Asp Val Glu  Glu Gln Asn Asn His  Arg Ser Val
        995                 1000                 1005

Leu Val  Ile Pro Glu Trp Glu  Ala Glu Val Ser Gln  Glu Val Arg
    1010                 1015                 1020

Val Cys  Pro Gly Arg Gly Tyr  Ile Leu Arg Val Thr  Ala Tyr Lys
    1025                 1030                 1035

Glu Gly  Tyr Gly Glu Gly Cys  Val Thr Ile His Glu  Ile Glu Asp
    1040                 1045                 1050

Asn Thr  Asp Glu Leu Lys Phe  Ser Asn Cys Val Glu  Glu Glu Val
    1055                 1060                 1065

Tyr Pro  Asn Asn Thr Val Thr  Cys Asn Asn Tyr Thr  Gly Thr Gln
    1070                 1075                 1080

Glu Glu  Tyr Glu Gly Thr Tyr  Thr Ser Arg Asn Gln  Gly Tyr Asp
    1085                 1090                 1095

Glu Ala  Tyr Gly Asn Asn Pro  Ser Val Pro Ala Asp  Tyr Ala Ser
    1100                 1105                 1110

Val Tyr  Glu Glu Lys Ser Tyr  Thr Asp Gly Arg Arg  Glu Asn Pro
    1115                 1120                 1125

Cys Glu  Ser Asn Arg Gly Tyr  Gly Asp Tyr Thr Pro  Leu Pro Ala
    1130                 1135                 1140

Gly Tyr  Val Thr Lys Asp Leu  Glu Tyr Phe Pro Glu  Thr Asp Lys
    1145                 1150                 1155

Val Trp  Ile Glu Ile Gly Glu  Thr Glu Gly Thr Phe  Ile Val Asp
    1160                 1165                 1170

Ser Val  Glu Leu Leu Leu Met  Glu Glu
    1175                 1180


<210> SEQ ID NO 2
<211> LENGTH: 634
<212> TYPE: PRT
<213> ORGANISM: Artificial Sequence
<220> FEATURE:
<223> OTHER INFORMATION: Cry-2-derived polypeptide

<400> SEQUENCE: 2

Met Gly Asn Ser Val Leu Asn Ser Gly Arg Thr Thr Ile Cys Asp Ala
1               5                   10                  15

Tyr Asn Val Ala Ala His Asp Pro Phe Ser Phe Gln His Lys Ser Leu
            20                  25                  30

Asp Thr Val Gln Arg Glu Trp Thr Glu Trp Lys Lys Asn Asn His Ser
        35                  40                  45

Leu Tyr Leu Asp Pro Ile Val Gly Thr Val Ala Ser Phe Leu Leu Lys
    50                  55                  60
```

-continued

```
Lys Val Gly Ser Leu Val Gly Lys Arg Ile Leu Ser Glu Leu Arg Asn
65                  70                  75                  80

Leu Ile Phe Pro Ser Gly Ser Thr Asn Leu Met Gln Asp Ile Leu Arg
                85                  90                  95

Glu Thr Glu Gln Phe Leu Asn Gln Arg Leu Asp Thr Asp Thr Leu Ala
            100                 105                 110

Arg Val Asn Ala Glu Leu Thr Gly Leu Gln Ala Asn Val Glu Glu Phe
        115                 120                 125

Asn Arg Gln Val Asp Asn Phe Leu Asn Pro Asn Arg Asn Ala Val Pro
    130                 135                 140

Leu Ser Ile Thr Ser Ser Val Asn Thr Met Gln Gln Leu Phe Leu Asn
145                 150                 155                 160

Arg Leu Pro Gln Phe Gln Met Gln Gly Tyr Gln Leu Leu Leu Leu Pro
                165                 170                 175

Leu Phe Ala Gln Ala Ala Asn Leu His Leu Ser Phe Ile Arg Asp Val
            180                 185                 190

Ile Leu Asn Ala Asp Glu Trp Gly Ile Ser Ala Ala Thr Leu Arg Thr
        195                 200                 205

Tyr Arg Asp Tyr Leu Lys Asn Tyr Thr Arg Asp Tyr Ser Asn Tyr Cys
    210                 215                 220

Ile Asn Thr Tyr Gln Ser Ala Phe Lys Gly Leu Asn Thr Arg Leu His
225                 230                 235                 240

Gly Thr Leu Glu Phe Arg Thr Tyr Met Phe Leu Asn Val Phe Glu Tyr
                245                 250                 255

Val Ser Ile Trp Ser Leu Phe Lys Tyr Gln Ser Leu Leu Val Ser Ser
            260                 265                 270

Gly Ala Asn Leu Tyr Ala Ser Gly Ser Gly Pro Gln Gln Thr Gln Ser
        275                 280                 285

Phe Thr Ser Gln Asp Trp Pro Phe Leu Tyr Ser Leu Phe Gln Val Asn
    290                 295                 300

Ser Asn Tyr Val Leu Asn Gly Phe Ser Gly Ala Arg Leu Ser Asn Thr
305                 310                 315                 320

Phe Pro Asn Ile Gly Gly Leu Pro Gly Ser Thr Thr Thr His Ala Leu
                325                 330                 335

Leu Ala Ala Arg Val Asn Tyr Ser Gly Gly Ile Ser Ser Gly Asp Ile
            340                 345                 350

Gly Ala Ser Pro Phe Asn Gln Asn Phe Asn Cys Ser Thr Phe Leu Pro
        355                 360                 365

Pro Leu Leu Thr Pro Phe Val Arg Ser Trp Leu Asp Ser Gly Ser Asp
    370                 375                 380

Arg Glu Gly Val Ala Thr Val Thr Asn Trp Gln Thr Glu Ser Phe Glu
385                 390                 395                 400

Thr Thr Leu Gly Leu Arg Ser Gly Ala Phe Thr Ala Arg Gly Asn Ser
                405                 410                 415

Asn Tyr Phe Pro Asp Tyr Phe Ile Arg Asn Ile Ser Gly Val Pro Leu
            420                 425                 430

Val Val Arg Asn Glu Asp Leu Arg Arg Pro Leu His Tyr Asn Glu Ile
        435                 440                 445

Arg Asn Ile Ala Ser Pro Ser Gly Thr Pro Gly Gly Ala Arg Ala Tyr
    450                 455                 460

Met Val Ser Val His Asn Arg Lys Asn Asn Ile His Ala Val His Glu
465                 470                 475                 480

Asn Gly Ser Met Ile His Leu Ala Pro Asn Asp Tyr Thr Gly Phe Thr
                485                 490                 495
```

-continued

```
Ile Ser Pro Ile His Ala Thr Gln Val Asn Asn Gln Thr Arg Thr Phe
            500                 505                 510

Ile Ser Glu Lys Phe Gly Asn Gln Gly Asp Ser Leu Arg Phe Glu Gln
        515                 520                 525

Asn Asn Thr Thr Ala Arg Tyr Thr Leu Arg Gly Asn Gly Asn Ser Tyr
    530                 535                 540

Asn Leu Tyr Leu Arg Val Ser Ser Ile Gly Asn Ser Thr Ile Arg Val
545                 550                 555                 560

Thr Ile Asn Gly Arg Val Tyr Thr Ala Thr Asn Val Asn Thr Thr Thr
                565                 570                 575

Asn Asn Asp Gly Val Asn Asp Asn Gly Ala Arg Phe Ser Asp Ile Asn
            580                 585                 590

Ile Gly Asn Val Val Ala Ser Ser Asn Ser Asp Val Pro Leu Asp Ile
        595                 600                 605

Asn Val Thr Phe Asn Ser Gly Thr Gln Phe Asp Leu Met Asn Thr Met
    610                 615                 620

Leu Val Pro Thr Asn Ile Ser Pro Leu Tyr
625                 630
```

<210> SEQ ID NO 3
<211> LENGTH: 2136
<212> TYPE: DNA
<213> ORGANISM: Bacillus thuringiensis

<400> SEQUENCE: 3

```
atggcttata ataataatca aaatcaatgc ataccttata attgtttgaa taatcccgaa     60

atcgaaatat tagaaggcgg aagaatatca gttggtaata ccccaattga tatttctctt    120

tcgcttactc agtttctttt gagtgaattt gtcccaggtg cggggtttgt attaggatta    180

attgatttaa tatggggatt tgtaggtcct tcccaatggg acgcatttct tgctcaagtg    240

gaacagttaa ttaaccaaag aatagcagaa gctgtaagaa atacagcaat tcaggaatta    300

gagggaatgg cacgggttta tagaacctat gctactgctt ttgctgagtg ggaaaaagct    360

cctgatgacc cagagctaag agaagcacta cgtacacaat ttacagcaac tgagacttat    420

ataagtggaa gaatatccgt tttaaaaatt caaacttttg aagtacagct gttatcagtg    480

tttgcccaag ctgcaaattt acatttatct ttattaagag acgttgtgtt ttttgggcaa    540

agatggggtt tttcaacgac aaccgtaaat aattactaca atgatttaac agaagggatt    600

agtacctata cagattatgc tgtacgctgg tacaatacgg gattagaacg tgtatgggga    660

ccggattcta gagattgggt aaggtataat caatttagaa gagaattaac actaactgta    720

ttagatatcg ttgctctgtt cccgaattat gatagtagaa gatatccaat tcgaacagtt    780

tcccaattaa caagagaaat ttatacaaac ccagtattag aaaattttga tggtagtttt    840

cgaggctcgg ctcagggcat agaaagaagt attaggagtc cacatttgat ggatatactt    900

aacagtataa ccatctatac ggatgctcat aggggttatt attattggtc agggcatcaa    960

ataatggctt ctcctgtcgg tttttcgggg ccagaattca cgtttccgct atatggaacc   1020

atgggaaatg cagctccaca acaacgtatt gttgcccaac taggtcaggg cgtgtataga   1080

acattatcct ctacttttta tagaagacct tttaatatag ggataaataa tcaacaacta   1140

tctgttcttg acgggacaga atttgcttat ggaacctcct caaatttgcc atccgctgta   1200

tacagaaaaa gcggaacggt agattcgctg gatgaaatac caccacagaa taacaacgtg   1260

ccacctaggc aaggatttag tcatcgatta agccatgttt caatgtttcg ttcaggctct   1320
```

-continued

```
agtagtagtg taagtataat aagagctcct atgttctctt ggatacatcg tagtgctgaa   1380

tttaataata taattgcatc ggatagtatt actcaaatcc ctgcagtgaa gggaaacttt   1440

ctttttaatg gttctgtaat ttcaggacca ggatttactg gtggggactt agttagatta   1500

aatagtagtg gaaataacat tcagaataga gggtatattg aagttccaat tcacttccca   1560

tcgacatcta ccagatatcg agttcgtgta cggtatgctt ctgtaacccc gattcacctc   1620

aacgttaatt ggggtaattc atccattttt tccaatacag taccagctac agctacgtca   1680

ttagataatc tacaatcaag tgattttggt tattttgaaa gtgccaatgc ttttacatct   1740

tcattaggta atatagtagg tgttagaaat tttagtggga ctgcaggagt gataatagac   1800

agatttgaat ttattccagt tactgcaaca ctcgaggctg aatataatct ggagagagcg   1860

cagaaggcgg tggatgcgct gtttacgtct acagaccaac tagggctaaa aacaaatgta   1920

acggattatc atattgatca agtgtccaat ttagttacgt gtttatcgga tgaatttggt   1980

ctggatgaaa agcgagaatt gtccgagaaa gtcaaacatg cgaagcgact cagtgatgaa   2040

cgcaatttac tccaagattc aaatttcaaa gacattaata ggcaaccaga acgtgggtgg   2100

ggcggaatta ctccttatgg aggaattagc ggctag                             2136
```

<210> SEQ ID NO 4
<211> LENGTH: 711
<212> TYPE: PRT
<213> ORGANISM: Bacillus thuringiensis

<400> SEQUENCE: 4

```
Met Ala Tyr Asn Asn Asn Gln Asn Gln Cys Ile Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240
```

-continued

```
Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Phe Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Ser Ser Val Ser Ile Ile Arg
        435                 440                 445

Ala Pro Met Phe Ser Trp Ile His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asp Ala Leu Phe Thr Ser Thr Asp Gln Leu Gly Leu Lys Thr Asn Val
625                 630                 635                 640

Thr Asp Tyr His Ile Asp Gln Val Ser Asn Leu Val Thr Cys Leu Ser
                645                 650                 655

Asp Glu Phe Gly Leu Asp Glu Lys Arg Glu Leu Ser Glu Lys Val Lys
```

-continued

```
        660                 665                 670

His Ala Lys Arg Leu Ser Asp Glu Arg Asn Leu Leu Gln Asp Ser Asn
    675                 680                 685

Phe Lys Asp Ile Asn Arg Gln Pro Glu Arg Gly Trp Gly Gly Ile Thr
    690                 695                 700

Pro Tyr Gly Gly Ile Ser Gly
705                 710
```

PROTEIN MIXTURES FOR MAIZE INSECT CONTROL

CROSS-REFERENCE TO RELATED APPLICATIONS

This application claims priority under 35 U.S.C. §119 to provisional application Ser. No. 61/146,875 filed Jan. 23, 2009, herein incorporated by reference in its entirety.

FIELD OF THE INVENTION

Embodiments of the present invention relate generally to the field of pest control, providing insecticidal polypeptides related to combinations of *Bacillus thuringiensis* (B.t.) Cry1 and Cry2 polypeptides and the polynucleotides that encode them. Embodiments of the present invention also relate to methods and compositions for improved resistance of plants to insect predation, including, but not limited to, transgenic plant production. The Cry1 and Cry2 polypeptide mixtures provide improved insecticidal activity and synergism against key plant pests, including maize pests.

BACKGROUND OF THE INVENTION

Numerous commercially valuable plants, including common agricultural crops, are susceptible to attack by insect and nematode pests, causing substantial reductions in crop yield and quality. For example, growers of maize (*Zea mays*), commonly referred to as corn in the United States, face a major problem with combating pest infestations. Insects, nematodes, and related arthropods annually destroy an estimated 15% of agricultural crops in the United States and an even greater percentage in developing countries. In addition, competition with weeds and parasitic and saprophytic plants account for even more potential yield losses. Yearly, such pests cause over $100 billion in crop damage in the United States alone.

In an effort to combat pest infestations, various methods have been employed in order to reduce or eliminate pests in a particular plot. These efforts include rotating corn with other crops that are not a host for a particular pest and applying pesticides to the above-ground portion of the crop, applying pesticides to the soil in and around the root systems of the affected crop. Traditionally, farmers have relied heavily on chemical pesticides to combat pest damage. However, the use of chemical pesticides is costly, as farmers apply billions of gallons of synthetic pesticides to combat these pests each growing season, costing nearly $8 billion. In addition, such pesticides are inconvenient for farmers, result in the emergence of insecticide-resistant pests, and they raise significant environmental and health concerns.

Because of concern about the impact of pesticides on public health and the health of the environment, significant efforts have been made to find ways to reduce the amount of chemical pesticides that are used. Recently, much of this effort has focused on the development of transgenic crops that are engineered to express insect toxicants derived from microorganisms. For example, U.S. Pat. No. 5,877,012 to Estruch et al. discloses the cloning and expression of proteins from such organisms as *Bacillus, Pseudomonas, Clavibacter* and *Rhizobium* into plants to obtain transgenic plants with resistance to such pests as black cutworms, armyworms, several borers and other insect pests. Publication WO/EP97/07089 by Privalle et al. teaches the transformation of monocotyledons, such as corn, with a recombinant DNA sequence encoding peroxidase for the protection of the plant from feeding by corn borers, earworms and cutworms. Jansens et al., *Crop Sci.,* 37(5):1616-1624 (1997), reported the production of transgenic corn containing a gene encoding a crystalline protein from Bt that controlled both generations of Eastern Corn Borer (ECB). U.S. Pat. Nos. 5,625,136 and 5,859,336 to Koziel et al. reported that the transformation of corn with a gene from Bt that encoded for a δ-endotoxin provided the transgenic corn with improved resistance to ECB. Additionally, a comprehensive report of field trials of transgenic corn that expresses an insecticidal protein from Bt has been provided by Armstrong et al., *Crop Science,* 35(2):550-557 (1995). For these and other reasons, there is a demand for alternative insecticidal agents for agricultural crops. For example, maize plants incorporating transgenic genes which cause the maize plant to produce insecticidal proteins providing protection from the target pest(s) is a more environmentally friendly approach to controlling pests. The use of pesticidal crystal proteins derived from the soil bacterium Bt commonly referred to as "Cry proteins" have been utilized. Cry proteins are globular protein molecules which accumulate as protoxins in crystalline form during late stage of the sporulation of Bt. After ingestion by the pest, the crystals are solubilized to release protoxins in the alkaline midgut environment of the larvae. Protoxins (~130 kDa) are converted into mature toxic fragments (~66 kDa N terminal region) by gut proteases. Many of these proteins are quite toxic to specific target insects, but harmless to plants and other non-targeted organisms. Some Cry proteins have been recombinantly expressed in crop plants to provide pest-resistant transgenic plants. Among those, Bt-transgenic cotton and corn have been widely cultivated.

A large number of Cry proteins have been isolated, characterized and classified based on amino acid sequence homology. See Crickmore et al., *Microbiol. Mol. Biol. Rev.,* 62:807-813 (1998). This classification scheme provides a systematic mechanism for naming and categorizing newly discovered Cry proteins. Bt toxins have traditionally been categorized by their specific toxicity towards specific insect categories. For example, the Cry1 group of toxins is toxic to Lepidoptera, and includes, but is not limited to, Cry1Aa, Cry1Ab and Cry1Ac. See Hofte et al., *Microbiol. Rev.,* 53:242-255 (1989). The Cry1 classification is the best known and contains the highest number of cry genes, currently totals over 130. Cry1 and Cry2 proteins share a minimal amount of sequence homology. See, e.g., Crickmore et al. (1998) indicating that Cry1A and Cry2A classes are among the most divergent.

It has generally been found that individual Cry proteins possess relatively narrow activity spectra. For example, Cry1Ac was the first toxin to be deployed in transgenic cotton for control of *H. virescens* and *H. zea* insect pests. This toxin is known for its high level toxicity to *H. virescens*. However, it is slightly deficient in its ability to control *H. zea* and has almost no activity on *Spodoptera* species. Additionally, Cry1Ab toxin has slightly less activity on *H. zea* than Cry1Ac but has far superior activity against *S. exigua.*

Cry2A is an exception as it is unusual in that this subset of Cry proteins possesses a broader effective range that includes toxicity to both the Lepidoptera and Diptera orders of insects. The Cry2A protein was discovered to be a toxin showing a dual activity against *Trichoplusia ni* (cabbage looper) and *Aedes taeniorhynchus* (mosquito) (Yamamoto & McLaughlin, *Biochem. Biophys. Res. Comm.,* 130:414-421 (1982)). The nucleic acid molecule encoding the Cry2A protein (termed Cry2Aa) was cloned and expressed in *B. megaterium* and found to be active against both Lepidoptera and Diptera insects (Donovan et al., *J. Bacteriol.,* 170:4732-4738 (1988)). An additional coding sequence homologous to Cry2Aa was cloned (termed Cry2Ab) and was found to be active only against Lepidoptera larvae (Widner & Whiteley, *J. Bacteriol.*, 171(2):965-974 (1989)).

Second generation transgenic crops could be more resistant to insects if they are able to express multiple, novel and/or synergistic Bt genes.

Accordingly, it is an objective of embodiments of the present invention to provide synergistic resistance to plant insects.

Another objective of embodiments of the invention includes methods for incorporating multiple Cry proteins into transgenic plants, namely maize.

SUMMARY OF THE INVENTION

Embodiments of the present invention relate to Cry polypeptides derived from Bt Cry1 and Cry2 polypeptides and provides a novel means for improved and synergistic insecticidal resistance against key crop pests. Embodiments of the present invention also relate to transgenic plants expressing such a nucleic acid and/or polypeptide. The transgenic plants can express the transgene in any way known in the art, including, but not limited to, constitutive expression, developmentally regulated expression, tissue specific expression, etc. Additionally, seed obtained from a transgenic plant of the invention is also encompassed.

BRIEF DESCRIPTION OF THE DRAWING

FIG. 1 shows the sequences for the IP1-88 and IP2-127 Cry proteins, as well as the DNA and amino acid sequence for a Cry1(h) protein relevant to the disclosure.

DETAILED DESCRIPTION

Unless defined otherwise, all technical and scientific terms used herein have the same meaning as commonly understood by one of ordinary skill in the art to which embodiments of this invention belong. Unless mentioned otherwise, the techniques employed or contemplated herein are standard methodologies well known to one of ordinary skill in the art. The materials, processes and examples described in the description are illustrative only and not intended to be limiting to the scope of the claims in any manner. Many modifications and other embodiments of the inventions set forth herein will come to mind to one skilled in the art to which these inventions pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims.

As used herein, "pesticidal agent" or "pesticide" includes any organism, organic substance, or inorganic substance that has pesticidal activity. As used herein, the term "pesticidal activity" refers to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. Preferably, pesticidal activity results in reduced damage to a plant with such a pesticidal agent as compared with plants lacking such pesticidal agent. If the pesticidal agent's target pest is an insect, it is referred to as an "insecticide." If the pesticidal agent's target pest is a mite, it is referred to as an "acaricide." If the pesticidal agent's target pest is a mite, it is referred to as a "nematicide". If the pesticidal agent's target pest is a fungus, it is referred to as a "fungicide." If the pesticidal agent's target pest is a bacterium, it is referred to as a "bactericide." If the pesticidal agent's target pest is a plant, it is referred to as a "herbicide."

Combinations of pesticidal agents can have one of three effects on pesticidal activity: antagonistic, additive, or synergistic. If the observed pesticidal activity of the two pesticidal agents together is approximately the expected pesticidal activity of the combination, the combination is said to be "additive." If the observed pesticidal activity of the two pesticidal agents together is less than the expected pesticidal activity of the combination, the combination is said to be "antagonistic." If the observed pesticidal activity of the two pesticidal agents together is greater than the expected pesticidal activity of the combination, the combination is said to be "synergistic." The expected pesticidal activity for a given combination of pesticidal agents is determined by the following method. If X is the observed level of pesticidal activity of pesticidal agent A alone and Y is the observed level of pesticidal activity of pesticidal agent B alone, the expected pesticidal activity of pesticidal agents A and B in combination (assuming the level of pesticidal activity is measured on a scale from 0 to 100) is $X+Y-(X*Y)/100$.

Embodiments of the invention may show an increase of pesticidal activity of a given combination of 1%, 2%, 3%, 4%, 5%, 6%, 7%, 8%, 9%, 10%, 15%, 20%, 25%, 30%, 35%, 40%, 45%, or 50% or greater against the insect target as compared to the expected pesticidal activity of the combination.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, as modified in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used, as described on the National Center for Biotechnology Information website. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. The term "equivalent program" as used herein refers to any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the Tm for the specific sequence at a defined ionic strength and pH. However, stringent conditions encompass temperatures in the range of about 1° C. to about 20° C. lower than the Tm, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The term "toxin" as used herein refers to a polypeptide showing pesticidal activity or insecticidal activity or improved pesticidal activity or improved insecticidal activity. "Bt" or "*Bacillus thuringiensis*" toxin is intended to include the broader class of Cry toxins found in various strains of Bt, which includes such toxins as, for example, Cry1s, Cry2s, or Cry3s.

The terms "proteolytic site" or "cleavage site" refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

Research has shown that the insect gut proteases of Lepidopterans include trypsins, chymotrypsins, and elastases. See, e.g., Lenz et al. (1991) *Arch. Insect Biochem. Physiol.* 16: 201-212; and Hedegus et al. (2003) *Arch. Insect Biochem. Physiol.* 53: 30-47. For example, about 18 different trypsins have been found in the midgut of *Helicoverpa armigera* larvae (see Gatehouse et al. (1997) *Insect Biochem. Mol. Biol.* 27: 929-944). The preferred proteolytic substrate sites of these proteases have been investigated. See, e.g., Peterson et al. (1995) *Insect Biochem. Mol. Biol.* 25: 765-774.

Efforts have been made to understand the mechanism of action of Bt toxins and to engineer toxins with improved properties. It has been shown that insect gut proteases can affect the impact of Bt Cry proteins on the insect. Some proteases activate the Cry proteins by processing them from a "protoxin" form into a toxic form, or "toxin." See Oppert (1999) *Arch. Insect Biochem. Phys.* 42: 1-12; Carroll et al. (1997) *J. Invertebrate Pathology* 70: 41-49. This activation of the toxin can include the removal of the N- and C-terminal peptides from the protein and can also include internal cleavage of the protein. Other proteases can degrade the Cry proteins. See Oppert, ibid.

A comparison of the amino acid sequences of Cry toxins of different specificities reveals five highly-conserved sequence blocks. Structurally, the toxins comprise three distinct domains which are, from the N- to C-terminus: a cluster of seven alpha-helices implicated in pore formation (referred to as "domain 1"), three anti-parallel beta sheets implicated in cell binding (referred to as "domain 2"), and a beta sandwich (referred to as "domain 3"). The location and properties of these domains are known to those of skill in the art. See, e.g., Li et al. (1991) *Nature,* 305:815-821; Morse et al. (2001) *Structure,* 9:409-417. When reference is made to a particular domain, such as domain 1, it is understood that the exact endpoints of the domain with regard to a particular sequence are not critical so long as the sequence or portion thereof includes sequence that provides at least some function attributed to the particular domain. Thus, for example, when referring to "domain 1," it is intended that a particular sequence includes a cluster of seven alpha-helices, but the exact endpoints of the sequence used or referred to with regard to that cluster are not critical. One of skill in the art is familiar with the determination of such endpoints and the evaluation of such functions.

In an effort to better characterize and improve Bt toxins, strains of the bacterium Bt have been studied. An effort was undertaken to identify the nucleotide sequences encoding the crystal proteins from the selected strains, and the wild-type (i.e., naturally occurring) nucleic acids of the embodiments were isolated from these bacterial strains, cloned into an expression vector, and transformed into *E. coli*. Depending upon the characteristics of a given preparation, it was recognized that the demonstration of pesticidal activity sometimes required trypsin pretreatment to activate the pesticidal proteins. Thus, it is understood that some pesticidal proteins require protease digestion (e.g., by trypsin, chymotrypsin, and the like) for activation, while other proteins are biologically active (e.g., pesticidal) in the absence of activation.

Such molecules may be altered by means described, for example, in U.S. application Ser. Nos. 10/606,320, filed Jun. 25, 2003, and 10/746,914, filed Dec. 24, 2003. In addition, nucleic acid sequences may be engineered to encode polypeptides that contain additional mutations that confer improved or altered pesticidal activity relative to the pesticidal activity of the naturally occurring polypeptide. The nucleotide sequences of such engineered nucleic acids comprise mutations not found in the wild type sequences.

The mutant polypeptides of the embodiments are generally prepared by a process that involves the steps of: obtaining a nucleic acid sequence encoding a Cry family polypeptide; analyzing the structure of the polypeptide to identify particular "target" sites for mutagenesis of the underlying gene sequence based on a consideration of the proposed function of the target domain in the mode of action of the toxin; introducing one or more mutations into the nucleic acid sequence to produce a desired change in one or more amino acid residues of the encoded polypeptide sequence; and assaying the polypeptide produced for pesticidal activity.

Many of the Bt insecticidal toxins are related to various degrees by similarities in their amino acid sequences and tertiary structure and means for obtaining the crystal structures of Bt toxins are well known. Exemplary high-resolution crystal structure solution of both the Cry3A and Cry3B polypeptides are available in the literature. The solved structure of the Cry3A gene (Li et al. (1991) Nature 353:815-821) provides insight into the relationship between structure and function of the toxin. A combined consideration of the published structural analyses of Bt toxins and the reported function associated with particular structures, motifs, and the like indicates that specific regions of the toxin are correlated with particular functions and discrete steps of the mode of action of the protein. For example, many toxins isolated from Bt are generally described as comprising three domains: a seven-helix bundle that is involved in pore formation, a three-sheet domain that has been implicated in receptor binding, and a beta-sandwich motif (Li et al. (1991) Nature 305: 815-821).

As reported in U.S. Pat. No. 7,105,332, and pending U.S. application Ser. No. 10/746,914, filed Dec. 24, 2003, the toxicity of Cry proteins can be improved by targeting the region located between alpha helices 3 and 4 of domain 1 of the toxin. This theory was premised on a body of knowledge concerning insecticidal toxins, including: 1) that alpha helices 4 and 5 of domain 1 of Cry3A toxins had been reported to insert into the lipid bilayer of cells lining the midgut of susceptible insects (Gazit et al. (1998) *Proc. Natl. Acad. Sci. USA* 95: 12289-12294); 2) the inventors' knowledge of the location of trypsin and chymotrypsin cleavage sites within the amino acid sequence of the wild-type protein; 3) the observation that the wild-type protein was more active against certain insects following in vitro activation by trypsin or chymotrypsin treatment; and 4) reports that digestion of toxins from the 3' end resulted in decreased toxicity to insects.

A series of mutations may be created and placed in a variety of background sequences to create novel polypeptides having enhanced or altered pesticidal activity. See, e.g., U.S. application Ser. Nos. 10/606,320, filed Jun. 25, 2003, now abandoned, and 10/746,914, filed Dec. 24, 2003. These mutants include, but are not limited to: the addition of at least one more protease-sensitive site (e.g., trypsin cleavage site) in the region located between helices 3 and 4 of domain 1; the replacement of an original protease-sensitive site in the wild-type sequence with a different protease-sensitive site; the addition of multiple protease-sensitive sites in a particular location; the addition of amino acid residues near protease-sensitive site(s) to alter folding of the polypeptide and thus enhance digestion of the polypeptide at the protease-sensitive site(s); and adding mutations to protect the polypeptide from degradative digestion that reduces toxicity (e.g., making a series of mutations wherein the wild-type amino acid is replaced by valine to protect the polypeptide from digestion). Mutations may be used singly or in any combination to provide polypeptides of the embodiments.

In this manner, the embodiments provide sequences comprising a variety of mutations, such as, for example, a mutation that comprises an additional, or an alternative, protease-sensitive site located between alpha-helices 3 and 4 of domain 1 of the encoded polypeptide. A mutation which is an additional or alternative protease-sensitive site may be sensitive to several classes of proteases such as serine proteases, which include trypsin and chymotrypsin, or enzymes such as elastase. Thus, a mutation which is an additional or alternative protease-sensitive site may be designed so that the site is readily recognized and/or cleaved by a category of proteases, such as mammalian proteases or insect proteases. A protease-sensitive site may also be designed to be cleaved by a particular class of enzymes or a particular enzyme known to be produced in an organism, such as, for example, a chymotrypsin produced by the corn earworm *Heliothis zea* (Lenz et al. (1991) *Arch. Insect Biochem. Physiol.* 16: 201-212). Mutations may also confer resistance to proteolytic digestion, for example, to digestion by chymotrypsin at the C-terminus of the peptide.

The presence of an additional and/or alternative protease-sensitive site in the amino acid sequence of the encoded polypeptide can improve the pesticidal activity and/or specificity of the polypeptide encoded by the nucleic acids of the embodiments. Accordingly, the nucleotide sequences of the embodiments can be recombinantly engineered or manipulated to produce polypeptides having improved or altered insecticidal activity and/or specificity compared to that of an unmodified wild-type toxin. In addition, mutations may be placed in or used in conjunction with other nucleotide sequences to provide improved properties. For example, a protease-sensitive site that is readily cleaved by insect chymotrypsin, e.g., a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be placed in a Cry background sequence to provide improved toxicity to that sequence. In this manner, the embodiments provide toxic polypeptides with improved properties.

For example, a mutagenized Cry nucleotide sequence can comprise additional mutants that comprise additional codons that introduce a second trypsin-sensitive amino acid sequence (in addition to the naturally occurring trypsin site) into the encoded polypeptide. An alternative addition mutant of the embodiments comprises additional codons designed to introduce at least one additional different protease-sensitive site into the polypeptide, for example, a chymotrypsin-sensitive site located immediately 5' or 3' of the naturally occurring trypsin site. Alternatively, substitution mutants may be created in which at least one codon of the nucleic acid that encodes the naturally occurring protease-sensitive site is destroyed and alternative codons are introduced into the nucleic acid sequence in order to provide a different (e.g., substitute) protease-sensitive site. A replacement mutant may also be added to a Cry sequence in which the naturally-occurring trypsin cleavage site present in the encoded polypeptide is destroyed and a chymotrypsin or elastase cleavage site is introduced in its place.

It is recognized that any nucleotide sequence encoding the amino acid sequences that are proteolytic sites or putative proteolytic sites (for example, sequences such as NGSR, RR, or LKM) can be used and that the exact identity of the codons used to introduce any of these cleavage sites into a variant polypeptide may vary depending on the use, i.e., expression in a particular plant species. It is also recognized that any of the disclosed mutations can be introduced into any polynucleotide sequence of the embodiments that comprises the codons for amino acid residues that provide the native trypsin cleavage site that is targeted for modification. Accordingly, variants of either full-length toxins or fragments thereof can be modified to contain additional or alternative cleavage sites, and these embodiments are intended to be encompassed by the scope of the embodiments disclosed herein.

It will be appreciated by those of skill in the art that any useful mutation may be added to the sequences of the embodiments so long as the encoded polypeptides retain pesticidal activity. Thus, sequences may also be mutated so that the encoded polypeptides are resistant to proteolytic digestion by chymotrypsin. More than one recognition site can be added in a particular location in any combination, and multiple recognition sites can be added to or removed from the toxin. Thus, additional mutations can comprise three, four, or more recognition sites. It is to be recognized that multiple mutations can be engineered in any suitable polynucleotide sequence; accordingly, either full-length sequences or fragments thereof can be modified to contain additional or alternative cleavage sites as well as to be resistant to proteolytic digestion. In this manner, the embodiments provide Cry toxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with wild-type toxins or by comparing mutant toxins which differ in their amino acid sequence. Putative proteolytic sites and proteolytic sites include, but are not limited to, the following sequences: RR, a trypsin cleavage site; LKM, a chymotrypsin site; and NGSR, a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Embodiments of the present invention provide insecticidal polypeptides related to Bt Cry1 and Cry2 polypeptides. Nucleic acid molecules encoding the polypeptides are also provided. Methods for using the polypeptides and nucleic acids to enhance resistance of plants to insect predation are encompassed.

The combination of a Cry1 and Cry2 protein yields a synergistic effect against a plurality of target pests, providing greater than expected mortality and/or resistance to a plurality of target pests. Prior art has in fact taught away from the disclosed embodiments, indicating that synergism is not an expected outcome for insecticidal activity. Others skilled in the art have indicated that such combinations result in the antagonism, rather than synergism, effect on *Helicoverpa armigera* (Liao, C. et al., Toxicity of *B. thuringiensis* insecticidal proteins of *Helicoverpa armigera* and *H. punctigera*, major pests of cotton, *J. Invertebrate Pathology* 80:55-63 (2002)). Others have found reported tests using Cry1 and Cry2 proteins with reported synergism effects (Ding et al., Expression and synergism of two cry insecticidal protein genes in *P. fluorescens, Chinese J. of Microbiol.,* 40:573-578 (2000)).

Methods of Enhancing Insect Resistance in Plants

Embodiments of the present invention provide methods of enhancing plant resistance to insect pests including, but not limited to, members of order Lepidoptera, the *Helicoverpa* ssp. (e.g., *Helicoverpa Zea* and *Heliothis virescens*), and/or *Spodoptera* ssp. (e.g., *Spodoptera exigua, Spodoptera frugiperda*) through the use of Cry1-derived insecticidal polypeptides combined with Cry2-derived insecticidal polypeptides to produce a synergistic effect. Any method known in the art can be used to cause the insect pests to ingest one or more polypeptides during the course of feeding on the plant. As such, the insect pest will ingest insecticidal amounts of the one or more polypeptides of embodiments of the invention and may discontinue feeding on the plant. In some embodiments, the insect pest is killed by ingestion of the one or more polypeptides. In other embodiments, the insect pests are inhibited or discouraged from feeding on the plant without being killed.

In one embodiment, transgenic plants can be made to express one or more polypeptides. The transgenic plant may express the one or more polypeptides in all tissues (e.g., global expression). Alternatively, the one or more polypeptides may be expressed in only a subset of tissues (e.g., tissue specific expression), preferably those tissues consumed by the insect pest. Polypeptides that are embodiments of the invention can be expressed constitutively in the plant or be under the control of an inducible promoter. Polypeptides that are embodiments of the invention may be expressed in the plant cytosol or in the plant chloroplast either by protein targeting or by transformation of the chloroplast genome.

In another embodiment, a composition comprising one or more polypeptides of embodiments of the invention can be applied externally to a plant susceptible to the insect pests. External application of the composition includes direct application to the plant, either in whole or in part, and/or indirect application, e.g., to the environment surrounding the plant such as the soil. The composition can be applied by any method known in the art including, but not limited to, spraying, dusting, sprinkling, or the like. In general, the composition can be applied at any time during plant growth. One skilled in the art can use methods known in the art to determine empirically the optimal time for administration of the composition. Factors that affect optimal administration time include, but are not limited to, the type of susceptible plant, the type of insect pest, which one or more polypeptides are administered in the composition.

The composition comprising one or more polypeptides may be substantially purified polypeptides, a cell suspension, a cell pellet, a cell supernatant, a cell extract, or a spore-crystal complex of Bt cells. The composition comprising one or more polypeptides embodying the invention may be in the form of a solution, an emulsion, a suspension, or a powder. Liquid formulations may be aqueous or non-aqueous based and may be provided as foams, gels, suspensions, emulsifiable concentrates, or the like. The formulations may include agents in addition to the one or more polypeptides embodying the invention. For example, compositions may further comprise spreader-sticker adjuvants, stabilizing agents, other insecticidal additives, diluents, agents that optimize the rheological properties or stability of the composition, such as, for example, surfactants, emulsifiers, dispersants, or polymers.

In another embodiment, recombinant hosts that express one or more polypeptides that are embodiments of the invention are applied on or near a plant susceptible to attack by an insect pest. The recombinant hosts include, but are not limited to, microbial hosts and insect viruses that have been transformed with and express one or more nucleic acid molecules (and thus polypeptides) of embodiments of the invention. In some embodiments, the recombinant host secretes the polypeptide into its surrounding environment so as to contact an insect pest. In other embodiments, the recombinant hosts colonize one or more plant tissues susceptible to insect infestation.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.), hereinafter "Sambrook". See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as 32P or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cry sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm (thermal melting point) can be approximated from the equation of Meinkoth and Wahl (1984) Anal. Biochem. 138: 267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, "% form" is the percentage of formamide in the hybridization solution, and L is the length of the hybrid in base pairs. The Tm is the temperature (under defined ionic strength and pH) at which 50% of a complementary target sequence hybridizes to a perfectly matched probe. Washes are typically performed at least until equilibrium is reached and a low background level of hybridization is achieved, such as for 2 hours, 1 hour, or 30 minutes.

Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm.

Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), the SSC concentration can be increased so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York). See also Sambrook. Thus, isolated sequences that encode a Cry protein of the embodiments and hybridize under stringent conditions to the Cry sequences disclosed herein, or to fragments thereof, are encompassed by the embodiments.

Preferably, a Cry1 and Cry2 polypeptide are produced by a transgenic plant, thereby making the plant resistant to attack from a target pest and providing synergistic resistance to at least one target pest. A discussion of production of such transgenic plants is provided below.

Production of Transgenic Plants

Any method known in the art can be used for transforming a plant or plant cell with a nucleic acid molecule of an embodiment of the present invention. Nucleic acid molecules can be incorporated into plant DNA (e.g., genomic DNA or chloroplast DNA) or be maintained without insertion into the plant DNA (e.g., through the use of artificial chromosomes). Suitable methods of introducing nucleic acid molecules into plant cells include microinjection (Crossway et al., *Biotechniques* 4:320-334 (1986)); electroporation (Riggs et al., *Proc. Natl. Acad. Sci.,* 83:5602-5606 (1986); D'Halluin et al., *Plant Cell,* 4:1495-1505 (1992)); *Agrobacterium*-mediated transformation (U.S. Pat. Nos. 5,563,055 and 5,981,840; Osjoda et al., *Nature Biotechnology,* 14:745-750 (1996); Horsch et al., *Science,* 233:496-498 (1984); Fraley et al., *Proc. Natl. Acad. Sci.,* 80:4803 (1983); Fütterer et al., *Gene transfer to plants,* 213-263 (Potrykus 1995); direct gene transfer (Paszkowski et al., *EMBO J.* 3:2717-2722 (1984)); ballistic particle acceleration (U.S. Pat. Nos. 4,945,050, 5,879,918, 5,886,244, and 5,932,782; Tomes et al., Direct DNA Transfer into Intact Plant Cells via Microprojectile Bombardment, *Plant Cell, Tissue, and Organ Culture: Fundamental Methods* (Gamborg & Phillips_1995); and McCabe et al., *Biotechnology,* 6:923-926 (1988)); virus-mediated transformation (U.S. Pat. Nos. 5,889,191, 5,889,190, 5,866,785, 5,589,367 and 5,316,931); pollen transformation (De Wet et al., *Experimental Manipulation of Ovule Tissues,* 197-209 (Chapman et al. 1985)); Lec 1 transformation (U.S. patent application Ser. No. 09/435,054; International Publication No. WO 00/28058); whisker-mediated transformation (Kaeppler et al., *Plant Cell Reports,* 9:415-418 (1990); Kaeppler et al., *Theor. Appl. Genet.,* 84:560-566 (1992)); and chloroplast transformation technology (Bogorad, *Trends in Biotechnology,* 18:257-263 (2000); Ramesh et al., *Methods Mol. Biol.,* 274:301-7 (2004); Hou et al., *Transgenic Res.,* 12:111-4 (2003); Kindle et al., *Proc. Natl. Acad. Sci.,* 88:1721-5 (1991); Bateman & Purton, *Mol Gen Genet.,* 263:404-10 (2000); Sidorov et al., *Plant J.,* 19:209-216 (1999)).

The choice of transformation protocols used for generating transgenic plants and plant cells can vary depending on the type of plant or plant cell, i.e., monocot or dicot, targeted for transformation. Examples of transformation protocols particularly suited for a particular plant type include those for: potato (Tu et al., *Plant Molecular Biology,* 37:829-838 (1998); Chong et al., *Transgenic Research,* 9:71-78 (2000)); soybean (Christou et al., *Plant Physiol.,* 87:671-674 (1988); McCabe et al., *BioTechnology,* 6:923-926 (1988); Finer & McMullen, *In Vitro Cell Dev. Biol.,* 27P:175-182 (1991); Singh et al., *Theor. Appl. Genet.,* 96:319-324 (1998)); maize (Klein et al., *Proc. Natl. Acad. Sci.,* 85:4305-4309 (1988); Klein et al., *Biotechnology,* 6:559-563 (1988); Klein et al., *Plant Physiol.,* 91:440-444 (1988); Fromm et al., *Biotechnology,* 8:833-839 (1990); Tomes et al., Direct DNA Transfer into Intact Plant Cells via Microprojectile Bombardment, *Plant Cell, Tissue, and Organ Culture: Fundamental Methods* (Gamborg & Phillips_ 1995)); and cereals (Hooykaas-Van Slogteren et al., *Nature* 311:763-764 (1984); U.S. Pat. No. 5,736,369).

In some embodiments, more than one construct is used for transformation in the generation of transgenic plants and plant cells. Multiple constructs may be included in cis or trans positions. In preferred embodiments, each construct has a promoter and other regulatory sequences. Embodiments of the invention relate to combinations of different Cry1 and Cry2 proteins resulting in a synergistic effect against target pests such as those disclosed herein. By way of example, the Cry1 protein may be the polypeptide disclosed in SEQ ID NO:1 or 4, or a polypeptide that is at least 90%, 91%, 92%, 93%, 94%, 95%, 96%, 97%, 98%, 99%, 99.5%, or 99.75% identical to the polypeptide of SEQ ID NO:1 or 4. By way of further example, the Cry2 protein may be the polypeptide disclosed in SEQ ID NO:2, or a polypeptide that is at least 90%, 91%, 92%, 93%, 94%, 95%, 96%, 97%, 98%, 99%, 99.5%, or 99.75% identical to the polypeptide of SEQ ID NO:2. As a result, a nucleic acid encoding such a Cry1 (such as, for example, the nucleic acid disclosed in SEQ ID NO:3) or Cry2 protein may be used in such a construct.

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in the art (e.g., Evans et al., *Protoplasts Isolation and Culture, Handbook of Plant Cell Culture,* 124-176 (MacMillilan Publishing Co. 1983); and *Binding, Regeneration of Plants, Plant Protoplasts,* 21-73 (CRC Press, 1985). Regeneration can also be obtained from plant callus, explants, organs, or parts thereof. Such regeneration techniques are also described in the art (e.g., Klee et al., *Ann. Rev. of Plant Phys.,* 38:467-486 (1987)).

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g. guard cells, egg cells, trichomes and the like), and progeny of same. The class of plants that can be used in embodiments of the present invention includes the class of higher and lower plants amenable to transformation techniques, including angiosperms (monocotyledonous and dicotyledonous plants), gymnosperms, ferns, and multicellular algae. Plants of a variety of ploidy levels, including aneuploid, polyploid, diploid, haploid and hemizygous plants are also included.

Embodiments of the invention may use nucleic acid molecules to confer desired traits on essentially any plant. Thus, embodiments of the invention have use over a broad range of plants, including species from the genera *Allium, Ananas, Anacardium, Apium, Arachis, Asparagus, Athamantha, Atropa, Avena, Bambusa, Beta, Brassica, Bromus, Browallia, Camellia, Cannabis, Carica, Ceratonia, Cicer, Chenopodium, Chicorium, Citrus, Citrullus, Capsicum, Carthamus, Cocos, Coffea, Coix, Cucumis, Cucurbita, Cynodon, Dactylis, Datura, Daucus, Dianthus, Digitalis, Dioscorea, Elaeis, Eliusine, Euphorbia, Festuca, Ficus, Fragaria, Geranium, Glycine, Graminae, Gossypium, Helianthus, Heterocallis, Hevea, Hibiscus, Hordeum, Hyoscyamus, Ipomoea, Lactuca, Lathyrus, Lens, Lilium, Linum, Lolium, Lotus, Lupinus, Lycopersicon, Macadamia, Macrophylla, Malus, Mangifera, Manihot, Majorana, Medicago, Musa, Narcissus, Nemesia, Nicotiana, Onobrychis, Olea, Olyreae, Oryza, Panicum, Panieum, Pannisetum, Petunia, Pelargonium, Persea, Pharoideae, Phaseolus, Phleum, Picea, Poa, Pinus, Pistachia, Pisum, Populus, Pseudotsuga, Pyrus, Prunus, Pseutotsuga, Psidium, Quercus, Ranunculus, Raphanus, Ribes, Ricinus, Rhododendron, Rosa, Saccharum, Salpiglossis, Secale, Senecio, Setaria, Sequoia, Sinapis, Solanum, Sorghum, Stenotaphrum, Theobromus, Trigonella, Trifolium, Triticum, Tsuga, Tulipa, Vicia, Vitis, Vigna*, and *Zea.*

In specific embodiments, transgenic plants are maize, potato, rice, soybean, alfalfa, sunflower, canola, or cotton plants.

Transgenic plants may be grown and pollinated with either the same transformed strain or different strains. Two or more generations of the plants may be grown to ensure that expression of the desired nucleic acid molecule, polypeptide and/or phenotypic characteristic is stably maintained and inherited. One of ordinary skill in the art will recognize that after the nucleic acid molecule of embodiments of the present invention is stably incorporated in transgenic plants and confirmed to be operable, it can be introduced into other plants by sexual crossing. Any of a number of standard breeding techniques can be used, depending upon the species to be crossed.

In certain embodiments the polynucleotides of the embodiments can be stacked with any combination of polynucleotide sequences of interest in order to create plants with a desired trait. For example, the polynucleotides of the embodiments may be stacked with any other polynucleotides encoding polypeptides having pesticidal and/or insecticidal activity, such as other Bt toxic proteins (described in, for example, U.S. Pat. Nos. 5,366,892; 5,747,450; 5,737,514; 5,723,756; 5,593,881; and Geiser et al., *Gene,* 48: 109 (1986)), lectins (Van Damme et al., *Plant Mol. Biol.,* 24: 825 (1994)), pentin (described in U.S. Pat. No. 5,981,722), and the like. The combinations generated can also include multiple copies of any one of the polynucleotides of interest. The polynucleotides of the embodiments can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al., *Eur. J. Biochem.,* 165: 99-106 (1987); and WO 98/20122) and high methionine proteins (Pedersen et al., *J. Biol. Chem.,* 261: 6279 (1986); Kirihara et al., *Gene,* 71: 359 (1988); and Musumura et al., *Plant Mol. Biol.,* 12: 123 (1989)); increased digestibility (e.g., modified storage proteins (U.S. Pat. No. 6,858,778); and thioredoxins (U.S. Pat. No. 7,009,087)); the disclosures of which are herein incorporated by reference in their entirety.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al., *Science,* 266: 789 (1994); Martin et al., *Science,* 262: 1432 (1993); Mindrinos et al., *Cell,* 78:1089 (1994)); acetolactate synthase (ALS) mutants that lead to herbicide resistance such as the S4 and/or Hra mutations; genes encoding resistance to inhibitors of glutamine synthase such as phosphinothricin or basta (e.g., bar or PAT genes); and glyphosate resistance (EPSPS and GAT (glyphosate acetyl transferase) genes (Castle et al., *Science,* 304:1151 (2004))); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., *J. Bacteriol.,* 170:5837-5847 (1988)) facilitate expression of polyhydroxyalkanoates (PHAs)); the disclosures of which are herein incorporated by reference. One could also combine the polynucleotides of the embodiments with polynucleotides providing agronomic traits such as male sterility (see, e.g., U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or over expression cassettes to generate the desired combination of traits in the plant. It is further recognized that polynucleotide sequences can be stacked at a desired genomic location using a site-specific recombination system. See, e.g., WO 99/25821, WO 99/25854, WO 99/25840, WO 99/25855, and WO 99/25853, all of which are herein incorporated by reference.

Determination of Expression in Transgenic Plants

Any method known in the art can be used for determining the level of expression in a plant of a nucleic acid molecule of embodiments of the invention or polypeptide encoded therefrom. For example, the expression level in a plant of a polypeptide encoded by a nucleic acid molecule of embodiments of the invention can be determined by immunoassay, quantitative gel electrophoresis, etc. Expression of nucleic acid molecules of embodiments of the invention can be measured directly by reverse transcription quantitative PCR (qRT-PCR) of isolated RNA from the plant. Additionally, the expression level in a plant of a polypeptide encoded by a nucleic acid molecule of embodiments of the invention can be determined by the degree to which the plant phenotype is altered. In one embodiment, enhanced insect resistance is the phenotype to be assayed.

As used herein, "enhanced insect resistance" refers to increased resistance of a transgenic plant expressing a polypeptide of an embodiment of the invention to consumption and/or infestation by an insect pest as compared to a plant not expressing a polypeptide of an embodiment of the invention. Enhanced resistance can be measured in a number of ways. In one embodiment, enhanced resistance is measured by decreased damage to a plant expressing a polypeptide of an embodiment of the invention as compared to a plant not expressing a polypeptide of an embodiment of the invention after the same period of insect incubation. Insect damage can be assessed visually. For example in cotton plants, damage after infestation can be measured by looking directly at cotton plant bolls for signs of consumption by insects. In another embodiment, enhanced resistance is measured by increased crop yield from a plant expressing a polypeptide of an embodiment of the invention as compared to a plant not expressing a polypeptide of an embodiment of the invention after the same period of insect incubation.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Lepidoptera.

Larvae of the order Lepidoptera include, but are not limited to, armyworms, cutworms, loopers, and heliothines in the family Noctuidae *Spodoptera frugiperda* J E Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia* elutella Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia* latiferreana Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermiiller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis* subflexa Guenée; *Malacosoma* spp. and *Orgyia* spp.

In particular embodiments, the insect pests are from the order of Lepidopteran insects including European corn borer, e.g., *Ostrinia nubilalis*; corn earworm, e.g., *Helicoverpa zea*; common stalk borer, e.g., *Papiapema nebris*; armyworm, e.g., *Pseudaletia unipuncta*; Southwestern corn borer, e.g., *Diatraea grandiosella*; black cutworm, e.g., *Agrotis ipsilon*; fall armyworm, e.g., *Spodoptera frugiperda*; beet armyworm, e.g., *Spodoptera exigua*; and diamond-back moth, e.g., *Plutella xylostella*. In specific embodiments, the insect pests are European corn borer, *Ostrinia nubilalis*, and corn earworm *Helicoverpa zea*.

Determinations can be made using whole plants, tissues thereof, or plant cell culture.

All publications and patent applications in this specification are indicative of the level of ordinary skill in the art to which embodiments of this invention pertain. All publications and patent applications are herein incorporated by reference to the same extent as if each individual publication or patent application was specifically and individually indicated by reference. The disclosure of each reference set forth herein is incorporated herein by reference in its entirety.

EXAMPLES

Embodiments of this invention can be better understood by reference to the following examples. The foregoing and following description of embodiments of the present invention and the various embodiments are not intended to limit the claims, but rather are illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

Example 1

The evaluation of potential synergism between Bt proteins IP1-88 (a Cry1) and IP2-127 (a Cry2) using the bioassay method according to Colby, S. R., Calculating synergistic and antagonistic responses of herbicide combinations, Weeds, 15(1):20-22 (1967). Bt proteins IP1-88 (a Cry1) and IP2-127 (a Cry2) were utilized as test substances to qualitatively confirm the presence and resultant effect of the Bt proteins. Evaluation of the interactive effects between the two insecticidal compounds was required to understand the effectiveness of the two toxins stacked in transgenic plants. Resultant synergy was examined using neonate larvae of European corn borer (ECB), *Ostrinia nubilalis*.

Standardized Lepidoptera LC50 diet incorporation bioassays were utilized to evaluate the effects of insecticidal proteins Cry1 and Cry2 on Lepidoptera larvae (referring to the immature stage of an insect between the egg and pupal stage of an insect with complete metamorphosis). All synergism experiments were conducted in completely randomized designs with 5 replications. Each replicate consisted of eight wells in a 96-well bioassay plate. There were two basic doses/treatments for each protein based on preliminary data, one close to but <LC50s based on mortality (M) data (as M1×), and the other close to but <IC50s based on response (R) data (as R1×, mortality+severe stunted or <0.1 mg/larva). Apart from the basic 1×:1× ratio, higher doses using 2× dose for one of the two proteins might be also used (1×:2× or 2×: 1×). The insecticidal proteins were combined with a Lepidoptera specific artificial diet to create the bioassay diet. Ingredients including boiling water, agar (SeaPlaque), agar (NuSeive), cooling water and Southland Premix were used for the diet. The diet was dispensed and combined with the proteins in 96-well plates and one neonate larva was placed in each well.

All plates in bioassays were placed in a growth chamber with a target temperature of 27±1° C. and relative humidity of >60%. Approximately 4 days after initiation of each bioassay, mortality and severe stunted (ss, <0.1 mg/larva) counts were scored. Data analysis was based on the following: X=Observed result from Compound A at dose p; Y=Observed result from Compound B at dose q; E=Expected result for mixture of A and B at dose (p+q) if there is no synergy or antagonism (assuming responses range from 0 to 100), whereby $E=X+(100-X)(Y/100)=X+Y-(X*Y)/100$; if observed value is greater than expected result (Obs>E): synergism; if observed value is similar as expected result (Obs=E): additive; and if observed value is less than expected result (Obs<E): antagonism. Results provided in Table 1 below showed synergism on ECB in the mixture of IP1-88 and IP2-127.

TABLE 1

Mortality of ECB caused by IP1-88 or IP2-127 alone and in mixture (n = 40, 4 d at 27° C.)

| Protein in single or combination | Dose | Observed % mortality* | Expected % mortality, Colby's equation |
|---|---|---|---|
| IP1-88 | M1x | 32.5 | — |
| | M2x | 23.1 | — |
| IP2-127 | M1x | 7.7 | — |
| | M2x | 20.5 | — |

TABLE 1-continued

| Mortality of ECB caused by IP1-88 or IP2-127 alone and in mixture (n = 40, 4 d at 27° C.) | | | |
|---|---|---|---|
| Protein in single or combination | Dose | Observed % mortality* | Expected % mortality, Colby's equation |
| IP1-88:IP2-127 | M1x:1x | 63.2 | 37.7 |
| | M1x:2x | 81.6 | 46.4 |
| | M2x:1x | 66.7 | 29.0 |

*Corrected data based on Abbott equation with CK mortality < 2.5%.

Example 2

Bt proteins IP1-88 (a Cry1) and IP2-127 (a Cry2), as well as additional proteins were utilized as test substances to further confirm the presence and resultant effect of the Bt proteins, according to the same methods of Example 1. Both European corn borers (ECB) and corn earworms (CEW), *Helicoverpa zea*, were used in the bioassays. The observed response (mortality+ss) of both ECB and CEW in two of three mixture treatments was evidently higher than expected mortality based on Colby's equation (results provided in Table 2), also indicative of synergism between IP1-88 and IP2-127 for both ECB and CEW.

TABLE 2

| Response (mortality + ss) of ECB and CEW caused by IP1-88 or IP2-127 alone and in mixture (n = 40, 4 d at 27° C.) | | | | |
|---|---|---|---|---|
| Protein in single or combination | Dose | Observed/expected % response | ECB | CEW |
| IP1-88 | R1x | Observed | 31.6 | 19.4 |
| | R2x | Observed | 94.5 | 27.8 |
| IP2-127 | R1x | Observed | 7.7 | 21.5 |
| | R2x | Observed | 20.5 | 83.8 |
| IP1-88:IP2-127 | R1x:1x | Observed | 94.7 | 86.8 |
| | | Expected | 36.9 | 36.7 |
| | R1x:2x | Observed | 76.9 | 94.7 |
| | | Expected | 45.6 | 86.9 |
| | R2x:1x | Observed | 66.7 | 68.4 |
| | | Expected | 94.9 | 36.7 |

Example 3

Bt proteins Cry1Ah and IP2-127 (a Cry2), as well as additional proteins were utilized as test substances to further confirm the presence and resultant effect of the Bt proteins, according to the same methods of Example 1. Both European corn borers (ECB) and corn earworms (CEW), *Helicoverpa zea*, were used in the bioassays. The observed mortality and response (mortality+ss) of both ECB and CEW in the mixture treatments was higher than expected based on Colby's equation (results provided in Table 3), also indicative of synergism between Cry1Ah and IP2-127.

TABLE 3

| Mortality (mort) and response (resp; mortality + ss) of ECB and CEW caused by Cry1Ah or IP2-127 alone and in mixture. | | | | | | | | | | |
|---|---|---|---|---|---|---|---|---|---|---|
| Protein in single | | Observed/expected | ECB - trial 1 | | CEW - trial 1 | | ECB - trial 2 | | CEW - trial 2 | |
| or combination | Dose | % response | % mort | % resp | % mort | % resp | % mort | % resp | % mort | % resp |
| Cry1Ah | R1x | Observed | 59.5 | 50.6 | 28.2 | 23.7 | 30.2 | 62.5 | 45.1 | 40.9 |
| | R2x | Observed | 77.2 | 92.2 | 66.7 | 44.7 | 30.2 | 75.0 | 70.9 | 70.4 |
| IP2-127 | R1x | Observed | 28.8 | 6.9 | 21.7 | 7.9 | 59.4 | 55.3 | 11.9 | 34.9 |
| | R2x | Observed | 72.6 | 33.3 | 26.3 | 34.2 | 67.7 | 73.3 | 42.4 | 62.7 |
| Cry1Ah: IP2-127 | R1x:1x | Observed | 74.0 | 65.4 | 69.9 | 69.5 | 77.0 | 92.9 | 62.8 | 72.9 |
| | | Expected | 71.2 | 54.0 | 43.8 | 29.7 | 71.6 | 83.2 | 51.6 | 61.5 |
| | R1x:2x | Observed | 92.2 | 82.0 | 74.0 | 65.8 | 93.4 | 100.0 | 79.7 | 96.6 |
| | | Expected | 88.9 | 67.1 | 47.1 | 49.8 | 77.5 | 90.0 | 68.4 | 78.0 |
| | R2x:1x | Observed | 92.2 | 75.4 | 81.4 | 62.2 | 54.1 | 89.7 | 86.9 | 90.2 |
| | | Expected | 83.8 | 92.7 | 73.9 | 49.1 | 71.6 | 88.8 | 74.4 | 80.8 |

(Trial 1: n = 40, trial 2: n = 32; both 4 d at 27° C.)

What is claimed is:

1. A method of reducing pest damage in a transgenic plant comprising:

planting a first transgenic plant seed, wherein the first transgenic plant seed comprises a first transgene and a second transgene, wherein the first transgene causes expression of a Cry1 protein in a plant, wherein the Cry1 protein is selected from the group consisting of (a) SEQ ID NO:1and (b) a polypeptide that is at least 99% identical to the amino acid sequence of SEQ ID NO:1, wherein said polypeptide has pesticidal activity; and the second transgene causes expression of a Cry2 protein in a plant, wherein the Cry2 protein is selected from the group consisting of (a) SEQ ID NO:2 and (b) a polypeptide that is at least 99% identical to the amino acid sequence of SEQ ID NO:2, wherein said polypeptide has pesticidal activity; thereby reducing damage caused by a first target pest to a plant grown from the first transgenic plant seed.

2. The method of claim 1 wherein the transgenic plant is maize.

3. The method of claim 1 wherein the first target pest is a member of order Lepidoptera.

4. The method of claim 3 wherein the first target pest is selected from the group consisting of European corn borer and corn earworm.

5. The method of claim 1 further comprising treating the first transgenic plant seed with a pesticidal agent.

6. The method of claim 5 wherein the pesticidal agent is selected from the group consisting of: an insecticide, an acaricide, a nematicide, a fungicide, a bactericide, a herbicide, or a combination thereof.

7. The method of claim 6 wherein the pesticidal agent is an insecticide.

8. The method of claim 7 wherein the insecticide is selected from the group consisting of: a pyrethrin, a synthetic pyrethrin, an oxadizine, a chloronicotinyl, a nitroguanidine, a triazole, an organophosphate, a pyrrol, a pyrazole, a phenol pyrazole, a diacylhydrazine, a biological/fermentation product, a carbamate, or a combination thereof.

9. The method of claim 1 wherein the first transgenic plant seed further comprises a herbicide resistance gene.

10. The method of claim 9 wherein the herbicide resistance gene is selected from the group consisting of: glyphosate N-acetyltransferase (GAT), 5-enolpyruvylshikimate-3-phosphate synthase (EPSPS), phosphinothricin N-acetyltransferase (PAT) or a combination thereof.

11. A method of reducing pest damage in a transgenic plant comprising:

planting a first transgenic plant seed, wherein the first transgenic plant seed comprises a first transgene and a second transgene, wherein the first transgene causes expression of a Cry1 protein in a plant and the second transgene causes expression of a Cry2 protein in a plant, the Cry1 protein comprising the polypeptide of SEQ ID NO:1 ; and the Cry2 protein comprising the polypeptide of SEQ ID NO: 2, thereby reducing damage caused by a first target pest to a plant grown from the first transgenic plant seed.

12. The method of claim 11 wherein the transgenic plant is maize.

13. The method of claim 11 wherein the first target pest is a member of order Lepidoptera.

14. The method of claim 13 wherein the first target pest is selected from the group consisting of European corn borer and corn earworm.

15. A transgenic plant comprising a first transgene and a second transgene, wherein the first transgene causes expression of a Cry1 protein in a plant and the second transgene causes expression of a Cry2 protein in a plant and wherein the Cry1 protein comprises the polypeptide of SEQ ID NO:1 and the Cry2 protein comprises the polypeptide of SEQ ID NO: 2.

* * * * *